US005719167A

United States Patent [19]
Doshi et al.

[11] Patent Number: 5,719,167
[45] Date of Patent: Feb. 17, 1998

[54] ANGIOSTATIC COMPOUNDS

[75] Inventors: Rupa Doshi, Fort Worth; Jon Nixon, Mansfield; Robert J. Collier, Jr., Arlington, all of Tex.

[73] Assignee: Alcon Laboratories, Inc., Fort Worth, Tex.

[21] Appl. No.: 511,944

[22] Filed: Aug. 7, 1995

[51] Int. Cl.$^6$ .................................................. A61K 31/34
[52] U.S. Cl. ........................................ 514/337; 514/469
[58] Field of Search ................................ 514/211, 337, 514/469

[56] References Cited

U.S. PATENT DOCUMENTS

| | | | |
|---|---|---|---|
| 3,476,777 | 11/1969 | Murakami et al. | 260/345.5 |
| 4,465,845 | 8/1984 | Okamoto et al. | 549/30 |
| 4,550,022 | 10/1985 | Garabedian et al. | |
| 4,912,102 | 3/1990 | Mohacsi et al. | 514/211 |
| 4,966,907 | 10/1990 | Caldwell et al. | 514/337 |
| 4,966,973 | 10/1990 | Goro et al. | 546/269 |
| 5,156,852 | 10/1992 | La Haye et al. | |
| 5,371,078 | 12/1994 | Clark et al. | |
| 5,424,321 | 6/1995 | Hellberg et al. | |
| 5,431,907 | 7/1995 | Abelson et al. | |

FOREIGN PATENT DOCUMENTS

| | | |
|---|---|---|
| 0354787 A1 | 2/1990 | European Pat. Off. |
| WO 91/06668 | 5/1991 | WIPO |
| WO 93/02192 | 2/1993 | WIPO |
| WO 93/16716 | 9/1993 | WIPO |
| WO 95/15958 | 6/1995 | WIPO |

OTHER PUBLICATIONS

Oikawa, et al., "Inhibition of angiogenesis by vitamin $D_3$ analogues", *European Journal of Pharmacology*, vol. 178, pp. 247–250 (1990).
Folkman, et al., "Angiogenic Factors", *Science*, vol. 235, pp. 442–447 (1987).
Furcht, "Critical Factors Controlling Angiogenesis: Cell Products, Cell Matrix, and Growth Factors", *Laboratory Investigation*, vol. 55, No. 5, pp. 505–509 (1986).
BenEzra, "Neovasculogenic Ability of Prostaglandins, Growth Factors, and Synthetic Chemoattractants", *American Journal of Ophthalmology*, vol. 86, No. 4, pp. 455–461 (1978).
Crum, et al., "A New Class of Steroids Inhibits Angiogenesis in the Presence of Heparin or a Heparin Fragment", *Science*, vol. 230, pp. 1375–1378 (1985).
Kitazawa, "Increased Intraocular Pressure Induced By Corticosteroids", *American Journal of Ophthalmology*, vol. 82, No. 3, pp. 492–495 (1976).
Taylor, et al., "Protamine is an inhibitor of angiogenesis", *Nature*, vol. 297, pp. 307–312 (1982).
Diaz-Flores, et al., "Angiogenesis: an update", *Histol Histopath*, vol. 9, pp. 807–843 (1994).
Seddon, J., et al., "Dietary Carotenoids, Vitamins A, C, and E, and Advanced Age-Related macular Degeneration", *Jama*, vol. 272, No. 18, pp. 1413–1420 (1994).

Freshney, R. I., *Culture of Animal Cells*, 3rd Edition, John Wiley and Sons, New York, NY, pp. 277–278 (1994).
McNatt, et al., "Angiostatic Activity And Metabolism Of Cortisol In The Chorioallantoic Membrane (CAM) Of The Chick Embryo", *Journal of Steriod Biochemistry and Molecular Biology*, vol. 42, No. 7, pp. 687–693 (1992).
BenEzar, D., et al., The Rabbit Cornea—A Model For The Study Of Angiogenic Factors, in Ocular Circulation and Neovascularization, *Documenta Opthalmalogia*, Proceedings Series 50, pp. 335–340 (1987).
BenEzar, D., "Thrombospondin and in Vivo Angiogenesis Induced by Basic Fibroblast Growth Factor or Lipopolysaccharide", *Investigative Opthalmology and Visual Sciences*, vol. 34, No. 13, pp. 3601–3608 (1993).
Cohen, N., et al., "Lewis Aid Mediated Nucleophilic Substitution Reactions of 2-Alkoyxy-3,4-dihydro-2H-1-benzopyrans: Regiochemistry and Utility in the Synthesis of 3,4-Dihydro-2H-1-benzopyran-2-carboxylic Acids", *Journal of Organic Chemistry*, vol. 54, pp. 3282–3292 (1989).
ElAttar, T. M., et al., "Vitamin E. Succinate Potentiates the Inhibitory Effect of Prostaglandins on Oral Squamous Carcinoma Cell Proliferation", *Prostaglandins Leukotrines and Essential Fatty Acids*, vol. 52, No. 1, pp. 69–73 (1995).
Fariss, M. W., et al., "The Selective Antiproliferative Effects of α-Tocopheryl Hemisuccinate and Cholesteryl Hemisuccinate on Murine Leukemia Cells Result from the Action f the Intact Compounds", *Cancer Research*, vol. 54, No. 13, pp. 3346–3351 (1994).
Bienfang, D. C., et al., Medical Progress—Ophthalmology, *New England Journal of Medicine*, vol. 323, pp. 956–967 (1990).
Billington, D., "Angiogenesis and its inhibition: potential new therapies in oncology and non-neoplastic diseases", *Drug Design and Discovery*, vol. 8, pp. 3–35 (1991).
Doctrow, S, et al., "Angiogenesis Modulators—New Drugs for Controlling Blood Vessel Growth?", *DN&P*, vol. 2, No. 2, pp. 74–81 (1989).
Kretzer, F., et al., "Vitamin E protects against retinopathy of prematurity through action on spindle cells", *Nature*, vol. 309, pp. 793–795 (1984).
Moses, M., et al., "Inhibitors of Angiogenesis", *Bio/Technology*, vol. 9, pp. 630–634 (1991).
Chemical Abstracts AN 1989:401445, Kanayasu et al., Jan. 1989.
Chemical Abstract AN 1994:427720, Tsopanoglou et al., Jan. 1994.
Chemical Abstracts AN 1988:422844, Eziri et al, WO 8705020.
Chemical Abstracts AN 1978:520777, Hiraishi et al, JP 53000126.
Chemical Abstracts AN 1969:38001, Miki et al, JP 43003780.

*Primary Examiner*—Keith MacMillan
*Attorney, Agent, or Firm*—Michael C. Mayo

[57] ABSTRACT

The present invention is directed to compositions containing angiostatic compounds and methods for their use in preventing pathological neovascularization.

10 Claims, No Drawings

ANGIOSTATIC COMPOUNDS

BACKGROUND OF THE INVENTION

The present invention relates to certain compounds useful in preventing and treating neovascularization. Specifically, the invention is directed to compositions containing chroman-type compounds and methods to treat neovascularization.

Angiogenesis is a term used to describe the development of new blood vessels or neovascularization (L. Diaz-Flores et al., *Angiogenesis: an Update, Histology and Histopathology*, volume 9, pages 807–843 (1994)). Though angiogenesis is a normal process for the development or maintenance of the vasculature, pathological conditions (i.e., angiogenesis dependent diseases) arise where blood vessel growth is actually harmful. Such pathologies include diabetic retinopathies, proliferative vitreoretinopathies, psoriasis, arthritis and tumor development. The progression of angiogenesis occurs in several phases which include: elaboration of the angiogenic signal; dissolution of the blood vessel basement membrane; endothelial cell proliferation; endothelial cell migration; and formation and differentiation of capillary tubules and loops. Each of these phases is a potential target for pharmacological intervention.

Tumor growth is dependent on neovascularization. For solid tumors to grow beyond the size of a pea, they must become vascularized. They do so by secreting their own angiogenic factor(s) which recruit new blood vessels to provide essential nutrients and oxygen.

Angiogenesis is also associated with other important diseases of ocular tissue especially in older patients and diabetics. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

Current therapy for the treatment of ocular neovascular disease is not very effective. Retinal neovascularization is often treated with multiple laser burns to the retina to remove the pathological vasculature. Patients with neovascular diseases of the anterior chamber (e.g. corneal neovascularization, iritis rubeosis) are treated with potent topical ocular glucocorticoids. These therapies are only partially effective and generally only slow neovascularization and the progress of the overall disease. In addition, they can cause severe side effects if used over a relatively long period of time.

Other attempts have been made to provide therapies for the prevention or treatment of pathological angiogenesis. For example, angiostatic steroids functioning to inhibit angiogenesis in the presence of heparin or specific heparin fragments are disclosed in Crum, et al., *A New Class of Steroids Inhibits Angiogenesis in the Presence of Heparin or a Heparin Fragment, Science*, volume 230, pages 1375–1378 (1985). Another group of angiostatic steroids useful in inhibiting angiogenesis is disclosed in commonly assigned U.S. Pat. No. 5,371,078 (Clark et al.).

Glucocorticoids, as mentioned above, have also been shown to inhibit angiogenesis. However, the use of glucocorticoid therapy in general is complicated by the inherent problems associated with steroid applications. Such problems include elevated intraocular pressure (Kitazawa, *Increased Intraocular Pressure Induced by Corticosteroids, American Journal of Ophthalmology*, volume 82, pages 492–493 (1976)).

Still other therapies have included: the use of protamine (S. Taylor, *Protamine is an Inhibitor of Angiogenesis, Nature*, volume 297, pages 307–312 (1982)); the use of calcitriol (*European Journal of Pharmacology*, volume 178, pages 247–250 (1990)); and the use of the antibiotic, fumagillin and its analogs, disclosed in EP 354787. The use of a variety of pharmaceutical proteins has also been proposed for treating angiogenesis. Such therapies have included: monoclonal antibodies directed to fibroblast growth factor, disclosed in WO 9106668; platelet factor 4, disclosed in WO 9302192; and thrombospondin fragments, disclosed in WO 9316716. Inherent in protein therapy, however, are problems of peptide stability, bioavailability and immunogenecity.

SUMMARY OF THE INVENTION

This invention is directed to compositions containing angiostatic compounds and methods of using these compositions to prevent and/or treat neovascularization in human patients. In particular, the compositions are useful for controlling ocular neovascularization.

The compositions of the present invention also have the advantage of providing effective angiostatic therapy which avoids the problems inherent in steroid and protein therapies.

DETAILED DESCRIPTION OF THE INVENTION

The compositions of the present invention contain compounds which have the general formula (I):

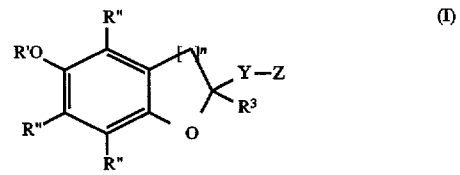

wherein:

n is 1 or 2;

R is H, $C_1$–$C_6$ alkyl or $C_3$–$C_6$ cycloalkyl;

Y is H, $C_1$–$C_6$ alkyl, $C_3$–$C_6$ cycloalkyl, O, NR, $C(R)_2$, CH(OH) or $S(O)_n$;

n' is 0 to 2;

R' is H, C(O)R, $C(O)N(R)_2$, $PO_3^-$, $SO_3^-$, or $HO_2C(CH_2)_2(C=O)$—;

R" is H or $C_1$–$C_6$ alkyl;

$R^3$ is H, $C_1$–$C_6$ alkyl, $(CH_2)_q(OH)$, —$(C=O)O(CH_2)_q CH_3$ or

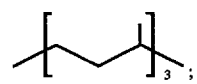

provided that R' can not be H, when $R^3$ is

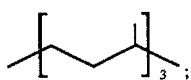

q is 1 to 10; and

Z, if present, is H, $C_1$–$C_6$ alkyl, $C_3$–$C_6$ cycloalkyl, or selected from the group consisting of:

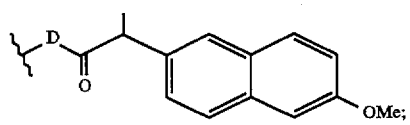

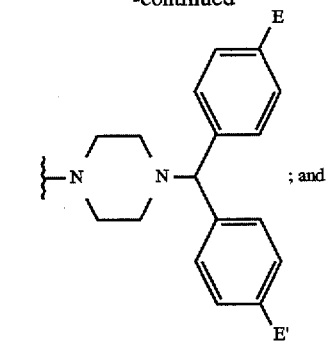

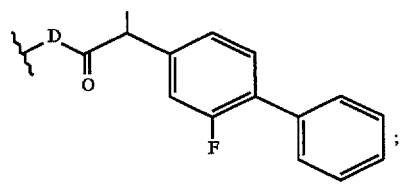

wherein:
D is O or NR; and
E and E' are independently H, F or Cl.

The compounds of the present invention also include pharmaceutically acceptable salts of the compounds of formula (I).

The following compounds are particularly preferred for use in the compositions and methods of the present invention:

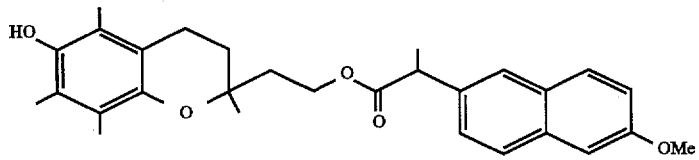

2-(6-hydroxy-2,5,7,8-tetramethyl-3,4-dihydro-2H-benzo[1,2-b]pyran-2-yl)ethyl 2-(6-methoxy-2-naphthyl)propionate ("Compound A";

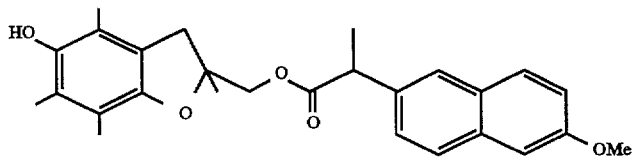

2-(5-hydroxy-2,4,6,7-tetramethyl-2,3-dihydro-benzo[1,2-b]furan-2-yl)methyl 2-(6-methoxy-2-naphthyl)propionate ("Compound B");

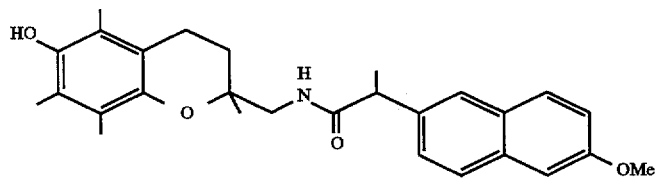

N-(2-(6-hydroxy-2,5,7,8-tetramethyl-3,4-dihydro-2H-benzo[1,2-b]pyran-2-yl)methyl)2-(6-methoxy-2-naphthyl)propionamide ("Compound C");

-continued

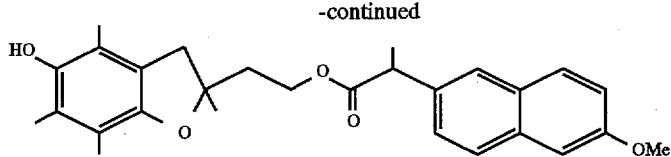

2-(5-hydroxy-2,4,6,7-tetramethyl-2,3-dihydro-benzo[1,2-b]furan-2-yl)ethyl 2-(6-methoxy-2-naphthyl)propionate ("Compound D");

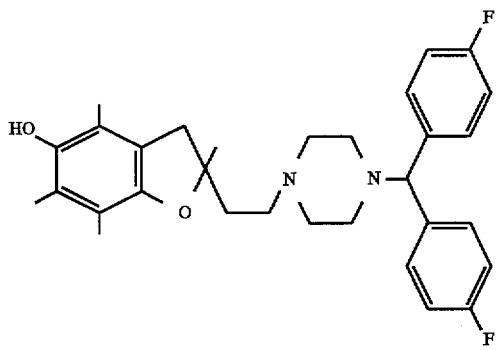

1-[2-(5-hydroxy-2,4,6,7-tetramethyl-2,3-dihydro-benzo[1,2-b]furan-2-yl)2-ethyl]-4-[4,4'-fluorobenzhydryl]piperzine ("Compound E")

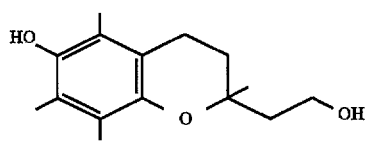

2-(6-hydroxy-2,5,7,8-tetramethyl-3,4-dihydro-2H-benzo[1,2-b]pyran-2-yl)ethanol ("Compound F")

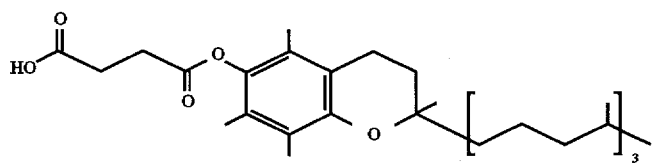

Vitamin E succinate (VES) ("Compound G")

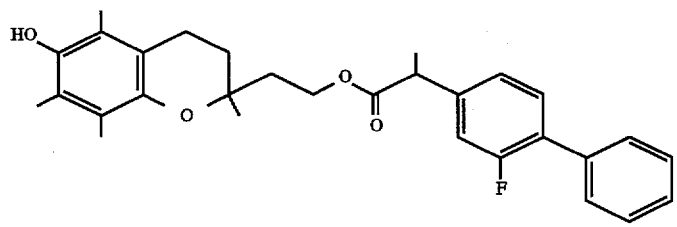

2-(6-hydroxy-2,5,7,8-tetramethyl-2,3-dihydro-2H-benzo[1,2-b]pyran-2-yl)ethyl 2-(3-fluoro-4-phenyl-phenyl)propionate ("Compound H").

The initiation of new blood vessel formation may arise quite differently in various tissues or as a result of different diseases. Many substances have been found to induce neovascularization, see, Folkman, et al., *Angiogenic Factors*, Science, volume 235, pages 442–447 (1987). However, it is believed, that once initiated, the process of neovascularization is similar in all tissues regardless of the associated disease, Furcht, *Critical Factors Controlling Angiogenesis: Cell Products, Cell Matrix, and Growth Factors*, Laboratory Investigation, volume 55, No. 5, pages 505–509 (1986).

There are many theories associated with the cause of neovascularization, and there may be different inducers depending on the disease or surgery involved, BenEzra, *Neovasculogenic Ability of Prostaglandins, Growth Factors, and Synthetic Chemoattractants*, American Journal of Ophthalmology, volume 86, No. 4, pages 455–461, (October, 1978). Regardless of the cause or the associated disease, it is believed that angiostatic agents work by inhibiting one or more steps in the process of neovascularization. Therefore, the angiostatic compounds of this invention are useful in the treatment and prevention of neovascularization associated with a variety of diseases and surgical complications.

The angiostatic compositions of the present invention are useful in inhibiting pathological neovascularization in human patients. As used herein, the term "pathological neovascularization" refers to those conditions where the formation of blood vessels (neovascularization) is harmful to the patient. Examples of pathological neovascularization dependent diseases include: head trauma, spinal trauma, systemic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, ocular neovascularization, nonunion fractures, Osler-Weber Syndrome, psoriasis, pyogenic granuloma, retrolental fibroplasia, pterigium, scleroderma, trachoma, vascular adhesions, and solid tumor growth.

In particular, the compositions are useful in preventing and treating any ocular neovascularization, including, but not limited to: retinal diseases (diabetic retinopathy, chronic glaucoma, retinal detachment, sickle cell retinopathy and subretinal neovascularization due to senile macular degeneration); rubeosis iritis; proliferative vitreoretinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insuffiency, choroidal thrombosis and carotid artery ischemia); pterigium; neovascularization of the optic nerve; and neovascularization due to penetration of the eye or contusive ocular injury.

The compounds of formula (I) may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; solutions and suspensions adapted for intra-vitreal or intra-cameral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. The ophthalmic compositions of the present invention will include one or more compounds of formula (I) and a pharmaceutically acceptable vehicle for said compound(s). Various types of vehicles may be used. The vehicles will generally be aqueous in nature. Aqueous solutions are generally preferred, based on ease of formulation, as well as a patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for compounds of formula (I) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0 percent by weight, based on the total weight of the composition (wt. %).

Some of the compounds of formula (I) may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2 wt. %.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 wt. %.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formula (I) to prevent or reduce angiogenesis in ophthalmic tissues is a particularly important aspect of the present invention. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compositions are administered intraocularly. As used herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference.

In general, the doses utilized for the above described purposes will vary, but will be in an effective amount to inhibit or reduce neovascularization. As used herein, the term "pharmaceutically effective amount" to inhibit or reduce neovascularization, is that amount which inhibits formation of new blood vessels or reduces the number of blood vessels which are involved in the pathological condition. The doses utilized for any of the above-described purposes will generally be from about 0.01 to about 100 milligrams per kilogram of body weight (mg/kg), administered one to four times per day. When the compositions are dosed topically, they will generally be in a concentration range of 0.001 to about 5 wt. %, with 1–2 drops administered 1–4 times per day.

The compositions of the present invention are further illustrated by the following examples.

EXAMPLE 1

Topical compositions useful for controlling ocular neovascularization:

| Component | wt. % |
| --- | --- |
| Angiostatic Compound | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 2

A preferred topical composition useful for controlling neovascularzation:

| Component | wt. % |
| --- | --- |
| Compound A | 1.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

Compound A is sterilized by either dry heat or ethylene oxide. If ethylene oxide sterilization is selected, aeration for at least 72 hours at 50° C. is necessary. The sterilized angiogenic compound is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 3

Formulation for oral administration:

Tablet:

10–1000 mg of an angiostatic compound with inactive ingredients such as starch, lactose and magnesium stearate can be formulated according to procedures known to those skilled in the art of tablet formulation.

EXAMPLE 4

Formulation for sterile intraocular injection:

| Component | each mL contains: |
| --- | --- |
| Angiostatic Compound | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide | q.s., pH to approx. 7.2 |
| Water for injection | q.s. |

EXAMPLE 5

Preferred formulation for a topical ocular solution:

| Component | wt. % |
| --- | --- |
| Compound A | 1.0% |
| Benzalkonium chloride | 0.01% |
| HPMC | 0.5% |
| Sodium chloride | 0.8% |
| Sodium phosphate | 0.28% |
| Edetate disodium | 0.01% |
| NaOH/HCl | q.s. pH 7.2 |
| Purified Water | q.s. 100 mL |

EXAMPLE 6

A preferred formulation for oral administration:

Tablet:

5–100 mg of Compound A with inactive ingredients such as starch, lactose and magnesium stearate can be formulated according to procedures known to those skilled in the art of tablet formulation.

The compositions and methods of the present invention are further illustrated by the following in vitro and in vivo biological activity examples of the compounds of formula (I):

EXAMPLE 7

Representative compounds of the present invention were assayed for their efficacy in inhibiting endothelial cell proliferation. Briefly, human umbilical vein endothelial cells (HUVEC) were seeded in 6-well plates at a density of 2500/cm2. At mid-log phase the cells were treated with a test compound or vehicle control. Forty-eight (48) hours later the cells were detached from the plate and counted using a coulter counter. Viability tests were conducted using trypan blue. The data is expressed as percent inhibition based on the control number of endothelial cells counted. The results are illustrated in Table 1 below:

TABLE 1

| Concentration [μM] | % Inhibition of Endothelial Cell Proliferation | | | | | |
|---|---|---|---|---|---|---|
| | Compound A | Compound B | Compound E | Vitamin E | Naproxen | Compound G |
| 1.0 | 6.7 | 5.0 | 25 | 0 | 0 | 4.3 |
| 5.0 | 25.5 | 13.9 | 48 | 0 | 1.9 | 8.0 |
| 10 | 43.4 | 47.7 | 88 | 1 | 1.0 | 35.1 |
| 25 | 55.2 | 60.5 | 91 | — | — | 65.5 |

The data of Table 2 demonstrates the endothelial cell anti-proliferative efficacy of representative compounds of the present invention, as compared to naproxen and vitamin E.

EXAMPLE 8

Representative compounds of the present invention were assayed for their efficacy in inhibiting $^3$H-thymidine uptake in DNA as a measure of DNA synthesis (R. I. Freshney, *Culture of Animal Cells*, 3rd Edition, John Wiley and Sons, N.Y., N.Y., pages 277–278 (1994)). Briefly, human lung microvascular endothelial cells in mid-log phase were exposed to either a representative compound of the present invention or the vehicle (1.0% DMSO) for 18 hours. Cells were then incubated with $^3$H-thymidine for another 6 hours. DNA synthesis was stopped by the addition of cold 5% TCA solution and the relative synthesis assessed by measuring $^3$H-thymidine incorporated into the acid-insoluble product. The data is expressed as percent inhibition of uptake based on tritium counts in the vehicle control reactions. The results are presented in Table 2 below:

TABLE 2

| Concentration [μM] | % Inhibition of $^3$H-thymidine Uptake | |
|---|---|---|
| | Compound A | Compound B |
| 5.0 | 16.3 | 36.9 |
| 10 | 25.7 | 63.1 |
| 15 | 57.4 | — |
| 20 | 82.9 | — |
| 25 | 96.5 | 97.9 |

The data of Table 2 demonstrates the efficacy of representative compounds of the present invention in inhibiting endothelial cell proliferation based on the inhibition of DNA synthesis.

EXAMPLE 9

Representative compounds of the present invention were assayed for their efficacy in inhibiting angiogenesis in a chorioallantoic membrane (CAM) model (See, McNatt, et al., *Angiostatic Activity and Metabolism of Cortisol in The Chorioallantoic Membrane (CAM) of the Chick Embryo, Journal of Steriod Biochemistry and Molecular Biology*, volume 42, No. 7, pages 687–693 (1992)). Briefly, 10 μg of the test compound or reference compound (tetrahydrocortisol) were suspended in a liposome/agarose bead and placed on the CAM of a 5–6 day chicken embryo. Following 2 days of incubation, the CAMs were scored for relative angiostatic activity by comparing percent responding embryos per nanomole test compound to percent responding embryos for the reference compound. The results are illustrated in Table 3 below:

TABLE 3

| Compound | RAF* |
|---|---|
| Tetrahydrocortisol | 1.00 (reference) |
| Compound A | 0.10 |
| Compound B | 1.06 |
| Compound E | 1.78 |
| Compound G | 1.21 |

*Relative Angiostatic Factor

As Table 3 demonstrates, representative compounds of the present invention show angiostatic efficacy in the CAM model.

EXAMPLE 10

Representative compounds of the present invention were assayed for their efficacy in inhibiting angiogenesis in vivo, in a rabbit model of lipopolysaccharide (LPS) induced corneal neovascularization. Briefly, the test compound and LPS (a stimulus for initiating neovascularization) are incorporated into separate Elvax-40 pellets as described in D. BenEzra, *The Rabbit Cornea, A Model for the Study of Angiogenic Factors*, in "Ocular Circulation and Neovascularization, *Documenta Opthalmalogia*, Proceedings Series 50, pages 335–340 (1987) and D. BenEzra, *Thrombospondin and In Vivo Angiogenesis to Induced by Basic Fibroblast Growth Factor or Lipopolysaccharide, Investigative Opthalmology and Visual Sciences*, volume 34, No. 13, pages 3601–3608 (1993), which are surgically implanted into rabbit cornea. The area covered by new vessel formation in response to LPS is measured and suppression of neovascularization by test compounds is estimated at the end of the test period. The data is expressed as a relative area units in relation to the Elvax control (100). The results are illustrated in Table 4 below:

TABLE 4

| | | | Relative Area of Neovascularization | | | |
|---|---|---|---|---|---|---|
| Days | Elvax control | Naproxen | Compound E | Compound A | Compound C | Hydrocortisone hemisuccinate | Compound F |
| 4 | 100 | 88 | 99 | 66 | 102 | 0 | 92 |
| 9 | 100 | 93 | 76 | 54 | 57 | 1.5 | 85 |
| 15 | 100 | 91 | 88 | 48 | 41 | 0.6 | 30 |
| 22 | 100 | 80 | 115 | 103 | 60 | 4.9 | 39 |

The data of Table 4 demonstrate the efficacy of representative compounds of the present invention in in vivo inhibition of neovascularization.

Some of the compounds of the present invention may contain a nonsteroidal anti-inflammatory agent (NSAIA) component, while others may contain a calcium channel blocker (flunarizine) component. These individual moieties may add additional pharmaceutical benefit to the angiostatic efficacy of the compounds of the present invention.

The compounds of the present invention are synthesized by known methods in the art. Compounds containing a non-steroidal anti-inflammatory agent (flurbiprofen or naproxen) can be made by methods illustrated in Scheme 1 and 2, and Examples 11–14. Compounds containing a flunarizine moiety may be made by methods disclosed in commonly assigned PCT Patent Publication No. WO/9515958, the entire contents of which are hereby incorporated by reference. Other compounds of the present invention are commercially available from: Sigma Chemical Co. (St. Louis, Mo.) and Aldrich Chemical Co. (Milwaukee, Wis.).

Scheme 1

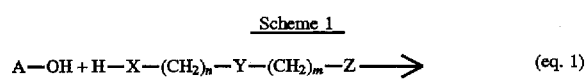

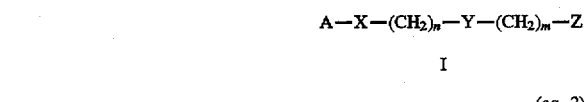

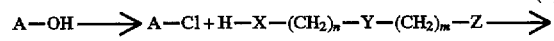

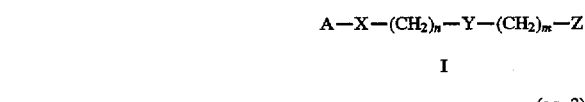

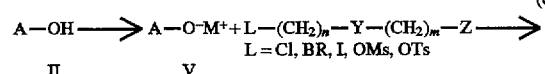

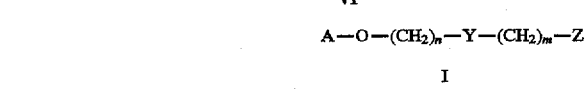

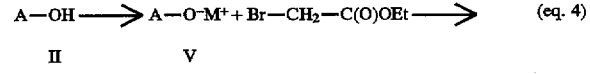

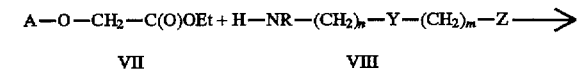

-continued
Scheme 1

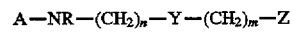

The conversion of the carboxylic acid containing nonsteroidal anti-inflammatory agents (II) to esters or amides (I) may be carried out by the following methods:

(i) As illustrated in equation 1 above, carboxylic acids (II) may be reacted with the appropriate amine or alcohol derivative (III) in the presence of a coupling reagent, such as dicyclohexylcarbodiimide or 1-(3-dimethylaminopropyl)-3-ethyl carbodiimide HCl, and 4-dimethylamine pyridine or 1-hydroxybenzotriazole, in an inert organic solvent, such as acetonitrile or tetrahydrofuran, and at a temperature from 0° C. to 50° C.

(ii) As illustrated in equation 2 above, carboxylic acids (II) may be converted to acid chlorides (IV) by reacting them with a reagent such as thionyl chloride or oxalyl chloride, in the presence of an inert solid or neat, at a temperature from 0° C. to 80° C. The resulting acid chloride (IV) may be reacted with the desired amine or alcohol (III) in an inert solvent such as tetrahydrofuran, in the presence of pyridine or a tertiary mine, such as triethylamine.

(iii) As illustrated in equation 3 above, esters (I) may be formed by reacting carboxylate anions (V), formed by reacting the carboxylic acid (II) with a base such as sodium hydride, with a halide (iodide, bromide, chloride) or sulfonate (mesylate, tosylate) (VI), in a solvent such as acetonitrile or dimethylformamide, at a temperature from 0° C. to 100° C.

(iv) As illustrated in equation 4 above, amides (I) may be prepared by reacting carboxylate anions (V), formed by reacting carboxylic acid (II) with a base such as sodium hydride, with ethyl bromoacetate. The resulting ester (VII) is reacted with the desired amine (VIII), neat or in an inert solvent, such as acetonitrile or dimethylformamide, at a temperature from 0° C. to 100° C.

The intermediate compounds (X) of Scheme 2 below, which can be used as compounds (III) and (VIII), were prepared using the general methods described in *Journal of Organic Chemistry*, volume 54, pages 3282–3292, (1989). The nitrile (IX) can be reduced using a reagent such as lithium aluminum hydride to afford the amine (X), which may be isolated as the hydrochloride salt.

The use of certain protecting groups and deprotection steps may be necessary, as will be appreciated by those skilled in the art.

Scheme 2

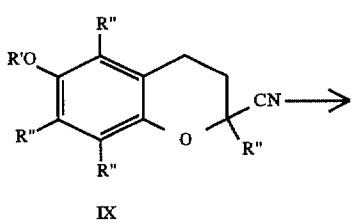

IX

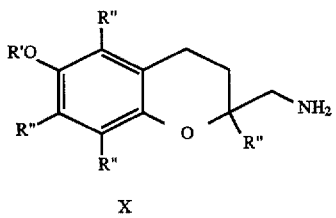

X

Compounds of formula (I) may exist as mixtures of stereoisomers. The preparation of the individual stereoisomers may be effected by preparing and resolving the acids (II), by known methods, and then using a single stereoisomer as starting material. Compounds (III), (VI) and (VIII) may be prepared as single stereoisomers from compounds of formula ($XI_{a-b}$), shown in Table 5 below, using known methods:

TABLE 5

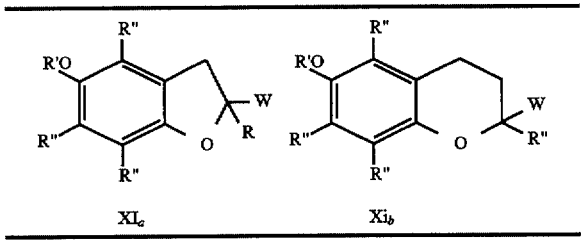

wherein:

W is $(CH_2)_p$-Q;
p is 0–1;
Q is $CH_2OH$ or $CO_2H$;
R' is H, C(O)R, C(O)$NR_2$, $PO_3^-$, or $SO_3^-$; and
R" is H or $C_1$–$C_6$ alkyl.

The alcohols ($XI_{a-b}$) may be resolved by forming esters with optically active carboxylic acids, separating the diastereomers, and then hydrolyzing the resolved diastereomers. The corresponding carboxylic acids ($XI_{a-b}$) may be resolved by forming an ester with an optically active alcohol, separating the diastereomers, and then hydrolyzing the resolved diastereomers. Or, the carboxylic acids ($XI_{a-b}$) may be resolved by forming an amine salt with an optically active amine. Separation by recrystallization and neutralization of the resolved carboxylic acid salt may be utilized to provide the resolved carboxylic acid. Resolution of the esters and amides (I) may also be effected using chromatographic techniques known to those skilled in the art.

The amines of formula (I), where Y is NR, may be converted to amine salts by reacting the amine with acids of sufficient strength to produce an organic or inorganic salt. The pharmaceutically acceptable anions include: acetate, bromide, chloride, citrate, maleate, fumarate, mesylate, phosphate, sulfate and tartrate.

Methods of synthesizing the compounds formula (I) are further illustrated by the following examples:

EXAMPLE 11

Synthesis of N-[(6-hydroxy-2,5,7,8-tetramethyl-3,4-dihydro-2H-1-benzo[1,2-b]pyran-2-yl)methyl]2-(6-methoxy-2-naphthyl)propionamide The intermediate, (6-hydroxy-2,5,7,8-tetramethyl-3,4-dihydro-2H-1-benzo[1,2-b]pyran-2-yl)methylamine, was first synthesized:

A 1 molar (M) ethereal solution of lithium aluminum hydride (Aldrich, 32.4 mL, 32.43 mmol) was added slowly over a 5 minute period to a chilled, (4°–6° C.) stirring solution of (2-cyano-6-hydroxy-2,5,7,8-tetramethyl-3,4-dihydro-2H-1-benzo[1,2-b]pyran in tetrahydrofuran (50 mL). After 2 hours, the reaction mixture was quenched by the slow sequential addition of 10% aqueous tetrahydrofuran (30 mL), 15% sodium hydroxide (10 mL) and then water (20 mL), while stirring. The resulting suspension was filtered through celite, and the celite pad was washed with ethyl ether (400 mL). The organic layer was separated, dried ($Na_2SO_4$), and concentrated in vacuo, resulting in a residue. A 1M ethereal solution of hydrochloride was then added to a solution of the residue in ethyl ether (100 mL), a solid formed, and the solid was then collected by filtration and washed with ethyl ether to give 2.31 g (65.4% yield) of a white solid. The product was used crude in the next reaction.

$^1$H-NMR (DMSO-$d_6$/TMS): 1.15 (s, 3H), 1.75 (t, 2H), 1.99 (s, 6H), 2.01 (s, 3H), 2.54 (t, 2H), 2.98 (s, 2H). MS (CI): 236 (m+1).

The hydrochloride salt of (6-hydroxy-2,5,7,8-tetramethyl-3,4-dihydro-2H-1-benzo[1,2-b]pyran-2-yl)methylamine (0.30 g, 1.10 mmole) and 6-methoxy-α-methyl naphthaleneacetic acid (Aldrich, 0.28 g, 1.21 mmole) were stirred in the presence of dimethylaminopyridine (Aldrich, 0.26 g, 2.20 mmole) and 1-(3-dimethylaminopropyl)-3-ethylcarbodiimide hydrochloride (Janssen Chimica-Spectrum, 0.21 g, 1.10 mmole), in tetrahydrofuran (4.0 mL) under an atmosphere of nitrogen. After stirring 17 hours at ambient temperature, the reaction mixture was diluted with ethyl acetate (70 mL), washed with water (2×15 mL), followed by brine (15 mL) and then dried (sodium sulfate). The mixture was concentrated in vacuo and the residue subjected to flash chromatography (silica gel, 100–50:0–50, v:v, hexanes:ethyl acetate). The appropriate fractions were concentrated in vacuo, and the resulting crystalline foam suspension was then washed in hexanes to give 0.28 g (58.3% yield) of N-[(5-hydroxy-2,5,7,8-tetramethyl-3,4-dihydro-2H-1-benzopyran-2-yl)methyl]-2-(6-methoxy-2-naphthyl)propionamide as a white amorphous solid.

$^1$H-NMR (CDCl$_3$) d 1.03–1.08 (d,3H), 1.57–1.64 (m, 6H), 1.70 (t, 2H,), 2.04–2.05 (m, 6H,), 2.48–2.51 (m, 2H),3.16–3.58 g (m, 2H),3.74(q, 1H),3.91 (s, 3H), 4.91 (br s, 1H), 5.751 (t, 1H), 7.01–7.19 (m, 2H), 7.29–7.40 (t, 1H), 7.52–7.81 (m, 3H). Elemental Analysis: Calculated for $C_{28}H_{33}NO_4$ Calculated: C, 75.14; H, 7.43; N, 3.13. Found: C, 75.04; H, 7.50; N, 2.97. Melting point: 67°–70° C.

EXAMPLE 12

Synthesis of 2-(6-hydroxy-2,5,7,8-tetramethyl-3,4-dihydro-2H-benzo [1,2-b]pyran-2yl)ethyl 2-(6-methoxy-2-naphthyl) propionate A solution of 1,3-dicyclohexylcarbodiimide (Aldrich, 0.89 g, 4.31 mmol) in acetonitrile (25 mL), was added dropwise to a stirring slurry of (+)-6-methoxy-a-methyl-2-5 naphthaleneacetic acid (Aldrich, 0.90 g, 3.91 mmol), 2-hydroxy-2,5,7,8-tetramethyl-3,4-dihydro-2H-benzo[1,2-b]pyran-2yl)ethanol (0.98 g, 3.91 mmol, U.S. Pat. No.

5,266,709 column 45) and 1-hydroxybenzotriazole hydrate (Aldrich, 0.59 g, 4.31 mmol), in acetonitrile (50 mL). After stirring for 18 hours, the reaction mixture was concentrated in vacuo. The residue was partitioned between water (30 mL) and methylene chloride (30 mL). The layers were separated, and the aqueous layer was extracted with methylene chloride (2×20 mL). The combined organic extracts were washed with water (20 mL), then dried (magnesium sulfate) and concentrated in vacuo. Flash chromatography (silica gel, 2:8, v:v, ethyl acetate:hexanes) of the residue afforded a white solid upon the concentration of the appropriate fractions. The white solid was recrystallized from an ethyl acetate-hexanes mixture to give 0.60 g (33.1% yield) of 2-(6-hydroxy-2,5,7,8-tetramethyl-3,4-dihydro-2H-benzo [1,2-b]pyran-2-yl)ethyl 2-(6-methoxy-2-naphthyl) propionate, a mixture of diastereomers, as a white solid.

$^1$N NMR (CDCl$_3$) d 1.1 (d, 3H), 1.6–1.5 (m, 3H), 1.6 (m, 2H), 1.9 (m,2H), 2.0 (s, 6H), 2.1 (s, 3H), 2.4 (t, 2H), 3.8 (q, 2H), 3.9 (s, 3H), 4.2 (s, 1H), 4.1–4.4 (m, 2H), 7.1–7.7 (m,6H). Elemental Analysis: Calculated for C$_{29}$H$_{34}$O$_5$ Calculated: C, 75.30; H, 7.41. Found: C, 75.24; H, 7.46. Melting Point: 99.5°–101.5° C.

EXAMPLE 13

Synthesis of 2-(5-hydroxy-2,4,6,7-tetramethyl-3,4-dihydrobenzo[1,2-b]furan-2yl)ethyl 2-(6-methoxy-2-naphthyl)propionate A solution of 2-(5-hydroxy-2,4,6,7-tetramethyl-2,3-dihydrobenzo[1,2-b]furan-2-yl)ethanol (1.30 g, 5.51 mmol) and 6-methoxy-α-methyl naphthaleneacetic acid (Aldrich, 1.39 g, 6.06 mmol) was stirred in the presence of dimethylaminopyridine (0.67 g, 5.51 mmol) and 1-(3-dimethylaminopropyl)-3-ethyl-carbodiimide hydrochloride (1.06 g, 5.51 mmol), in tetrahydrofuran (25 mL). The reaction mixture was stirred at ambient temperature under nitrogen for 24 hours, diluted with ethyl acetate (150 mL), washed with water (2×40 mL) and then brine (30 mL). The organic extract was dried (sodium sulfate) and concentrated in vacuo. The residue was subjected to flash chromatography (silica gel, 100–50:0–50, v:v, hexanes:ethyl acetate), and the appropriate fractions were combined to give 1.84 g (74.5% yield) of a foam residue. Fractional crystallization and recrystallization from methylene chloride-hexanes gave 0.40 g (13.0% yield) of white solid.

$^1$H-NMR (CDCl$_3$): 1.34 (s, 3H), 1.54–1.57 (d, 3), 1.99 (t, 2H), 2.01 (s, 3H), 2.05 (s, 3H), 2.10 (s, 3), 2.73–2.81 (d, 1), 2.90–2.97 (d, 1), 3.77–3.89 (q, 1H), 3.91 (s, 3H), 4.102 (s, 1H, 4.165–4.29 (m, 2H), 7.10–7.16 (m, 2H), 7.35–7.40 (m, 1H), 7.64–7.70 (m, 2H). Elemental Analysis: Calculated for C$_{28}$H$_{32}$O$_5$.0.1 mole CH$_2$Cl$_2$. Calculated: C, 73.84; H, 7.10. Found: C, 73.85, 73.83; H, 7.12. Melting point: 129.5°–131° C.

EXAMPLE 14

Synthesis of 2-(6-hydroxy-2,5,7,8-tetramethyl-3,4-dihydro-2H-benzo [1,2-b]pyran-2yl)ethyl 2-(3-fluoro-4-phenyl-phenyl)propionate The intermediate, 2-(6-benzyloxy-2,5,7,8-tetramethyl-3,4-dihydro-2H-benzo[1,2-b]pyran-2yl)ethyl 2-(3-fluoro-4-phenyl-phenyl)propionate, was first synthesized: A solution of flubiprofen (Sigma, 2.0 g, 8.2 mmol), 2-(6-benzyloxy-2,5,7,8-tetramethyl-3,4-dihydro-2H-benzo[1,2-b]pyran-2-yl) ethanol (2.4 g, 8.2 mmol) 1-hydroxybenzotriazole hydrate (Aldrich, 2.4 g, 13.9 mmol) and 1-(3-dimethylaminopropyl) -3-ethyl-carbodiimide hydrochloride (Aldrich, 2.8 g, 12.3 mmol), in acetonitrile (40 ml), was stirred at ambient temperature. After 72 hours, the reaction mixture was concentrated in vacuo and the residue partitioned between water and methylene chloride. A solid formed which was removed by filtration and discarded. The layers were separated and the aqueous layer was extracted with methylene chloride (2×25 ml). The combined organic extracts were then dried (magnesium sulfate) and concentrated in vacuo. The residue was chromatographed (silica gel, 2:8, v:v, ethyl acetate:hexane). Concentration of the appropriate fractions afforded 3.0 g (64% yield, mixture of stereoisomers) of the product as a clear oil.

$^1$H NMR (CDCl$_3$) d: 1.23–1.27 (m, 3H), 1.53–1.57 (m, 3H), 1.75 (m, 2H), 1.95 (m, 2H), 2.08 (s, 3H), 2.14 (s, 3H), 2.21 (s, 3H), 2.55 (t, 3H), 3.75 (m, 2H), 4.3 (m, 1H), 4.65 (s, 2H), 7.1–7.7 (m, 13H).

A solution of 2-(6-benzyloxy-2,5,7,8-tetramethyl-3,4-dihydro-2H-benzo [1,2-b]pyran-2yl)ethyl 2-(3-fluoro-4-phenyl-phenyl)propionate in ethyl acetate was treated with 10% palladium on charcoal (Aldrich, 0.5 g). The resulting mixture was hydrogenated on a Parr Apparatus [initial pressure 60 pounds/inch$^2$ (psi)]. After 18 hours, the reaction mixture was filtered, and the resulting solution concentrated in vacuo. The residue was subjected to flash chromatography (silica gel, 2:8, v:v, ethyl acetate:hexane). Concentration of the appropriate fractions afforded a clear oil. Hexane was added to the oil and a white solid formed upon standing. The white solid was collected by filtration to afford 0.91 g (36% yield) of 2-6-hydroxy-2,5,7,8-tetra methyl-,4-dihydro-H-benzo[1,2-b]pyran-yl)ethyl 2-(3-fluoro-4-phenyl-phenyl) propionate as a mixture of stereoisomers.

$^1$H NMR (CDCl$_3$) d: 1.22–1.23 (m, 3H), 1.51–1.55 (m, 3H), 1.65–1.8 (m, 2H), 1.85–2.00 (m, 2H),2.08 (s, 6H),2.14 (s, 3H),2.57 (t, 2H),3.75 (q, 1H), 4.1–4.5 (m, 2H), 7.10–7.65 (m, 8H). Elemental Analysis: Calculated for C$_{30}$H$_{33}$FO$_4$. Calculated: C,75.60; H, 6.98. Found: C,75.69; H,7.01. Melting point: 85°–87° C.

The invention in its broader aspects is not limited to the specific details shown and described above. Departures may be made from such details within the scope of the accompanying claims without departing from the principles of the invention and without sacrificing its advantages.

What is claimed is:

1. A method for treating pathological neovascularization which comprises administering to a human patient an effective amount of a pharmaceutical composition comprising a compound according to formula (I):

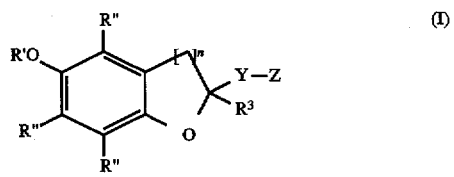

wherein:

n is 1 or 2;

R is H, C$_1$–C$_6$ alkyl or C$_3$–C$_6$ cycloalkyl;

Y is H, C$_1$–C$_6$ alkyl, C$_3$–C$_6$ cycloalkyl, O, NR, C(R)$_2$, CH(OH) or S(O)$_n$;

n' is 0 to 2;

R' is H, C(O)R, C(O)N(R)$_2$, PO$_3^-$, SO$_3^-$ or HO$_2$C(CH$_2$)$_2$ (C=O)—;

R" is H or C$_1$–C$_6$ alkyl;

R$^3$ is H, C$_1$–C$_6$ alkyl, (CH$_2$)$_q$(OH), —(C=O)O(CH$_2$)$_q$ CH$_3$ q is 1 to 10; and Z, if present, is H, $C_1$–$C_6$ alkyl, $C_3$–$C_6$ cycloalkyl, or selected from the group consisting of:

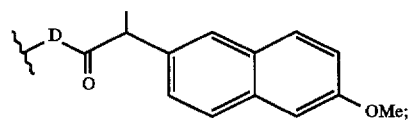

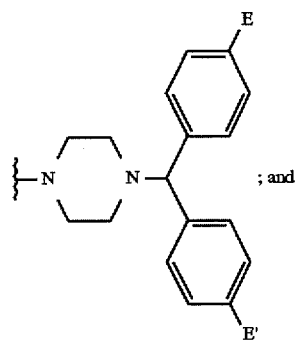

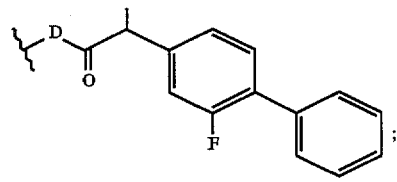

wherein:

D is O or NR; and

E and E' are independently H, F or Cl; and pharmaceutically acceptable salts thereof.

2. The method according to claim 1, wherein: R is H, R' is H; R" is $CH_3$; $R^3$ is $CH_3$; and Y is $C_1$–$C_2$ alkyl.

3. The method according to claim 1, wherein Z is:

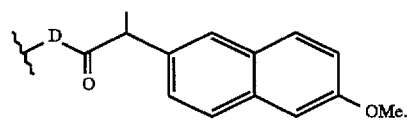

4. The method according to claim 1, wherein Z is:

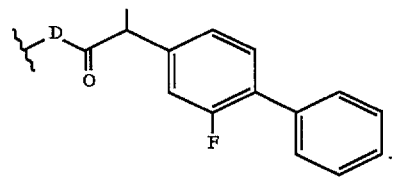

5. The method according to claim 1, wherein Z is:

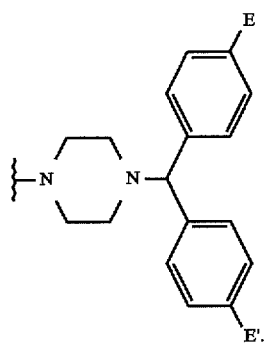

6. The method according to claim 2, wherein Z is:

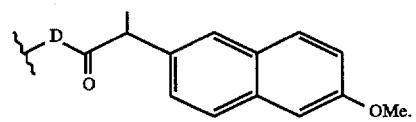

7. The method according to claim 2, wherein Z is:

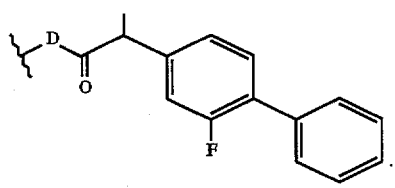

8. The method according to claim 2, wherein Z is:

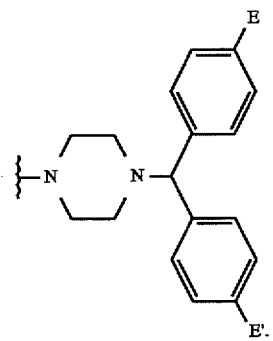

9. The method according to claim 1, wherein the compound is selected from the group consisting of:

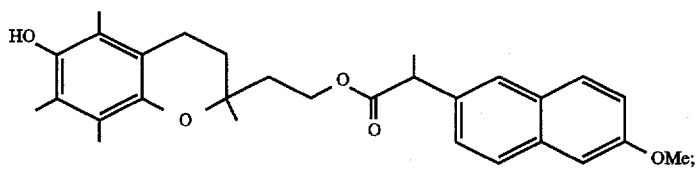
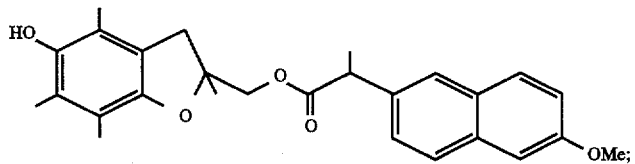
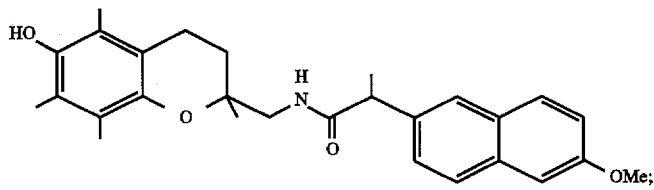
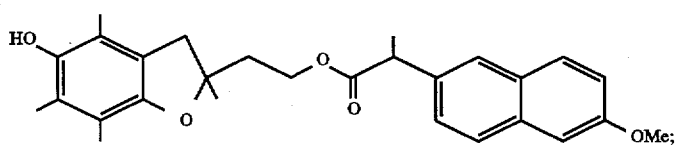
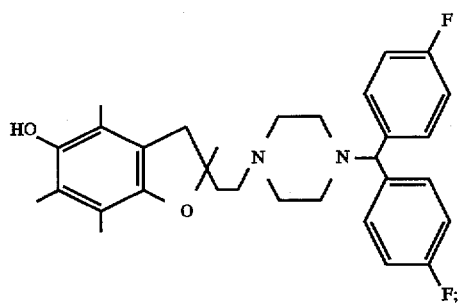
and
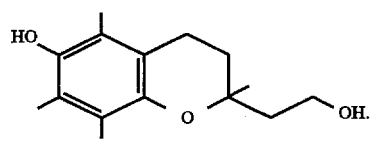
10. The method according claim 1, wherein the composition comprises a physiologically balanced irrigating solution.
* * * * *